(12) United States Patent
Rose (10) Patent No.: US 7,621,896 B2
(45) Date of Patent: Nov. 24, 2009

(54) DEVICE FOR SECURING INTRAVENOUS NEEDLES TO TREATMENT SITES

(76) Inventor: Shirley Ann Rose, 647 106th Ave. North, Naples, FL (US) 34108

(*) Notice: Subject to any disclaimer, the term of this patent is extended or adjusted under 35 U.S.C. 154(b) by 0 days.

(21) Appl. No.: 10/341,163

(22) Filed: Jan. 13, 2003

(65) Prior Publication Data
US 2004/0138623 A1 Jul. 15, 2004

(51) Int. Cl.
*A61M 5/00* (2006.01)
(52) U.S. Cl. .................................................. 604/174
(58) Field of Classification Search .................. 604/29, 604/165.03, 174, 177, 179, 539, 513, 180; 128/DIG. 6, DIG. 26, 846, 869, 870, 876–879; 602/60–62, 20, 23; 2/16, 20, 460, 455, 24
See application file for complete search history.

(56) References Cited

U.S. PATENT DOCUMENTS

| | | | | |
|---|---|---|---|---|
| 1,772,922 A * | 8/1930 | Volz | ................. | 2/22 |
| 2,727,512 A * | 12/1955 | Muller | .................. | 604/180 |
| 3,888,244 A * | 6/1975 | Lebold | .................. | 602/4 |
| 3,942,525 A * | 3/1976 | Dragan | .................. | 602/60 |
| 4,120,052 A * | 10/1978 | Butler | .................. | 2/16 |
| 4,333,181 A * | 6/1982 | Corriero | .................. | 2/24 |
| 4,531,942 A * | 7/1985 | Turner | .................. | 604/180 |
| 4,707,861 A * | 11/1987 | Lavoie et al. | .................. | 2/16 |
| 4,862,904 A * | 9/1989 | West et al. | .................. | 128/877 |
| 4,905,715 A * | 3/1990 | Johnson | .................. | 128/882 |
| 5,336,195 A * | 8/1994 | Daneshvar | .................. | 604/179 |
| 5,472,413 A * | 12/1995 | Detty | .................. | 602/26 |
| 5,577,516 A * | 11/1996 | Schaeffer | .................. | 128/877 |
| 5,643,216 A * | 7/1997 | White | .................. | 604/174 |
| 5,983,408 A * | 11/1999 | Li | .................. | 2/455 |
| 6,374,408 B1 * | 4/2002 | Tomlinson et al. | .................. | 2/22 |
| 6,375,639 B1 * | 4/2002 | Duplessie et al. | .................. | 604/174 |
| 6,402,712 B1 * | 6/2002 | Gauvry | .................. | 602/26 |
| 6,504,078 B2 * | 1/2003 | Vokal | .................. | 602/42 |
| 6,849,056 B1 * | 2/2005 | Wiggins et al. | .................. | 602/21 |

* cited by examiner

*Primary Examiner*—Nicholas D Lucchesi
*Assistant Examiner*—Christopher D Koharski
(74) *Attorney, Agent, or Firm*—Isaac A. Angres (57) ABSTRACT

The invention is directed to a system and device for securing one or more intravenous needles or cannulas to a patient in a treatment site such as on an arm, hand or leg. The device includes a semi-rigid but flexible pad that is placed in a location which is opposite of the treatment site, such as on the opposite side of an arm, hand or leg. The pad has straps emanating from it which extend around the patient and while doing so cross each other to trap a needle or cannula stabilizing feature and then continue around the patient and back to the pad. The pad has a first part of a hook and loop fastening system thereon, while the straps have the second part of the hook and loop fastening system thereon so that when engaged they will securely hold the straps in place. The pads may take on different shapes such as rectangular, oval or triangular shape to be able to be placed at different locations on the patient.

1 Claim, 7 Drawing Sheets

DEVICE FOR SECURING INTRAVENOUS NEEDLES TO TREATMENT SITES

CROSS REFERENCE TO RELATED APPLICATIONS (none)

STATEMENT REGARDING FED SPONSORED R & D (none)

FIELD OF THE INVENTION

The present invention relates generally to medical devices and particularly to a device for securing intravenous needles, cannulas and tubing to treatment sites including arterial-venous fistula sites as used in dialysis treatment.

BACKGROUND OF THE INVENTION

Intravenous needles and cannulas, also referred to as venous access devices, must be secured to patients to prevent dislodgment during medical treatment. The term needle will be used herein to refer to both needles and cannulas. The location of the needle insertion point or points on a patient vary with the type of medical treatment and the location of a suitable vein. Such locations include for example an upper arm, a surface on the outside surface of a hand, a wrist of a hand, a lower arm or an inside of an elbow of an arm. In dialysis treatment, a special site is typically created to provide for a strengthened vein, most commonly in the forearm and less frequently in the leg, to repeatedly accept two large needles and provide for sufficient flow of blood. The special site is created by joining a vein and an artery and is called a fistula and receives two arterial-venous (AV) fistula needles. In any of the above mentioned locations, it is very difficult to keep the needle secured to operate satisfactorily. In dialysis treatment, where the treatment is prolonged, repeated frequently, and two large needles are used, the problem of securing the needles is exasperated.

It is of the utmost importance that the needle or needles be kept under surveillance to check for proper operation and potential dislodgment or leaks of fluid. The most prevalent method to secure needles is to apply adhesive bandages and/or tape to keep the needles in place. Unfortunately, bandages and tape can frequently obscure the view of the needle insertion point and needle assembly. Furthermore, many patients cannot tolerate prolonged or repeated applications of adhesive bandages and tape to their skin and have or develop an allergic reaction to adhesive bandages and tape. It has been known that patients who undergo dialysis treatments several times a week for a prolonged period of time can exhibit blue and black spots on their skin because of such an allergy to the adhesive and the continuous application thereof. Other solutions such as arm boards with straps around the location of the needle to keep it in place are not satisfactory because they severely restrict the movement of the patient. What is needed is a device that secures one or more intravenous needles, such as two arterial-venous fistula needles, securely in place, provides for observance of the treatment location, allows for some movement of the patient and does not require adhesive bandages.

SUMMARY OF THE INVENTION

The invention at hand solves the above noted problems. In the securement of the needles or a needle in either a dialysis or other intravenous (IV) procedure, no adhesives are used. Once a needle is placed within a vein, the needle is kept in place by straps that cross each other in that particular location. The straps are derived from and are fixed to a pad that is placed on an opposite side of the limb, hand or other part of the patient's body to which the needle is located. As the straps are moved around the location of the needle, they will cross that location and will return to their origin of the other side of the pad and will be fastened thereto. More than one strap will cross each other at the needle to thereby securely hold the needle in place at that location. A first strap can be used to apply a first pressure to secure the needle. A second strap can be used to apply a second pressure to further secure the needle.

DETAILED DESCRIPTION OF THE INVENTION

Figure 1:
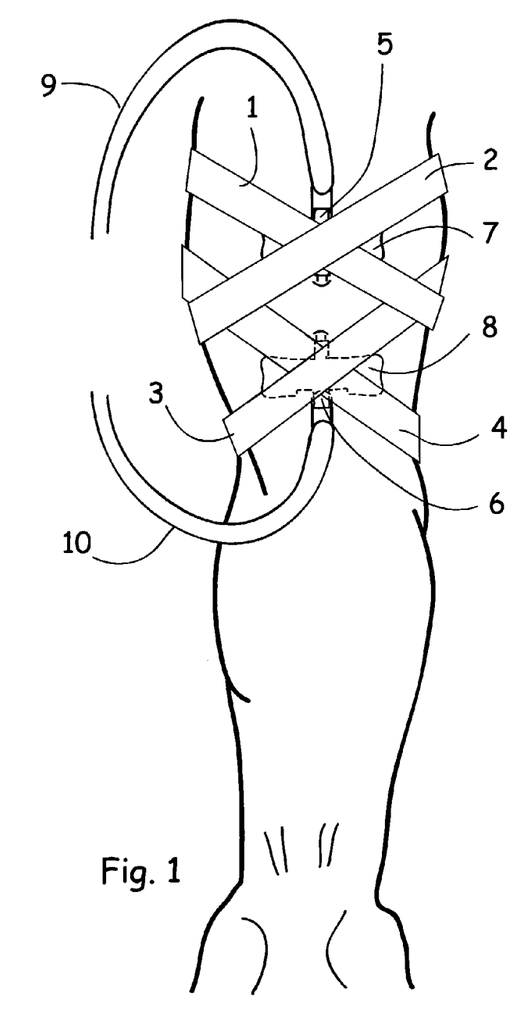
FIG. 1 shows a double needle, such as two arterial-venous fistula needles, secured on an inside of an arm.
Figure 2:
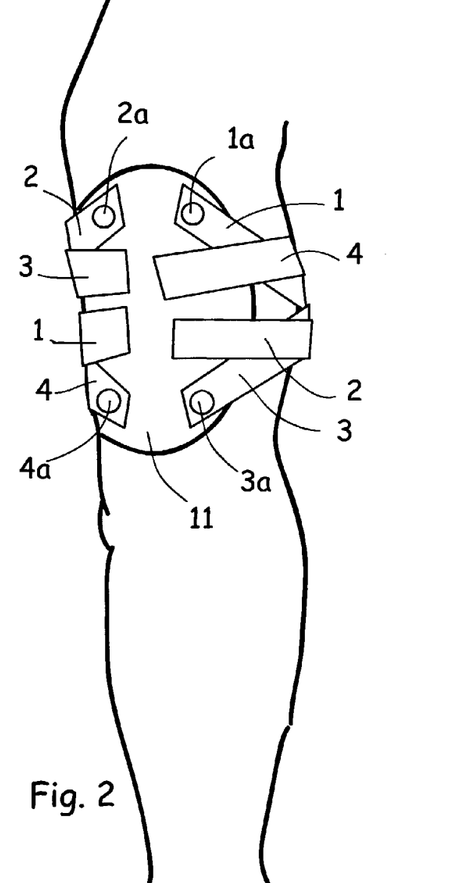
FIG. 2 shows the location of a pad on the outside of an arm from which straps will come forward to cross a needle.

FIGS. 1 and 2 illustrate how the present invention is applied to an inner surface of an upper arm of a patient to secure two intravenous (IV) needles 5 and 6, such as two arterial-venous (AV) fistula needles. Needles 5 and 6 respectively have tubes 9 and 10 and tabs, also called wings, 7 and 8 attached thereto to form needle assemblies also referred to herein as needle assemblies 9 and 10, respectively. The embodiment depicted in FIGS. 1 and 2 employs four straps 1, 2, 3 and 4 to hold the two needles in place. In the orientation shown in FIGS. 1 and 2, straps 1 and 2 are upper straps and straps 3 and 4 are lower straps. Strap 1 is fastened to an oval pad 11 by way of a grommet 1a. Grommet 1a should be fastened in such a way so that the strap 1 can rotate relative to the pad 11 and can follow the angle of direction to which the strap 1 is forced when it is applied thereby preventing kinks. This is also true for grommets 2a, 3a and 4a which fasten straps 2, 3 and 4 to the pad 11 respectively. The pad 11 is applied to the outer arm if the locations if the needles 5 and 6 are applied to the inner arm. In this application, the upper straps 1 and 2 cross each other over the upper needle 5 and return to the pad 11 where both of the straps are fastened to the pad 11 by way of the well known hook and loop fastening system, VELCRO™. This is equally true for the lower straps 3 and 4 which cross each other over the lower needle 6. This way the upper straps 1 and 2 and the lower straps 3 and 4 can each be individually adjusted to properly fit over the tab 7 of upper needle assembly 9 and tab 8 of lower needle assembly 10, respectively. The needles 5 and 6 are held in place by crossing straps 1 and 2, and 3 and 4, over tabs 7 and 8, respectively. The needles are thereby securely fastened without adhesive bandages, the injection points and treatment sites are easily observed, and the patient has some ability for movement.

Figure 3:
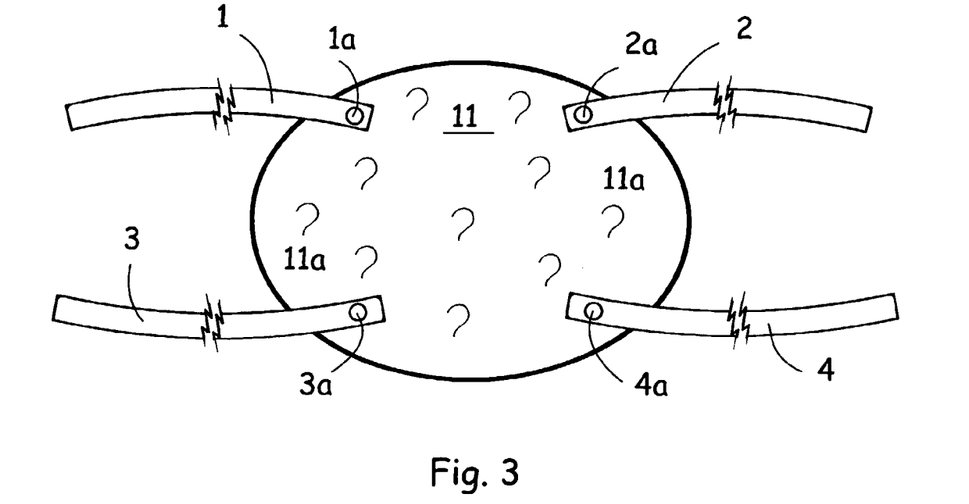
FIG. 3 illustrates a typical pad, such as that depicted in FIG. 2, having straps thereon and how they are fastened thereto.

FIG. 3 shows the pad 11 of FIGS. 1 and 2 when it is not applied to a patient. The pad 11 has hooks 11a of the VEL­CRO™ system on an outer surface as indicated in FIG. 3. The four straps 1, 2, 3 and 4 are fastened to the pad 11 at 1a, 2a, 3a, and 4a by grommets that are applied in such a manner so that the straps are able to rotate into the direction by which they are forced by the application of the pad and the location of the needles themselves. Straps 1, 2, 3 and 4 have loops of the VELCRO™ system applied to the surface facing pad 11 (not shown), which also faces the patient when the device is applied. The loops of the VELCRO™ system tend to be softer and more compliant than the hooks. Thus patient comfort can be improved with this arrangement of the hooks and loops. Furthermore, the more compliant loops will better conform to the tabs 7 and 8 thereby providing for good retention thereof. Alternatively, the outer surface of the pad 11 could have the loops thereon so that the VELCRO™ system cannot snag on any outer garment. However, this arrangement would require the hooks to be applied to straps 1, 2, 3 and 4 and the previ­ously mentioned patient comfort and tab retention may be lessened as a result.

Figure 4:
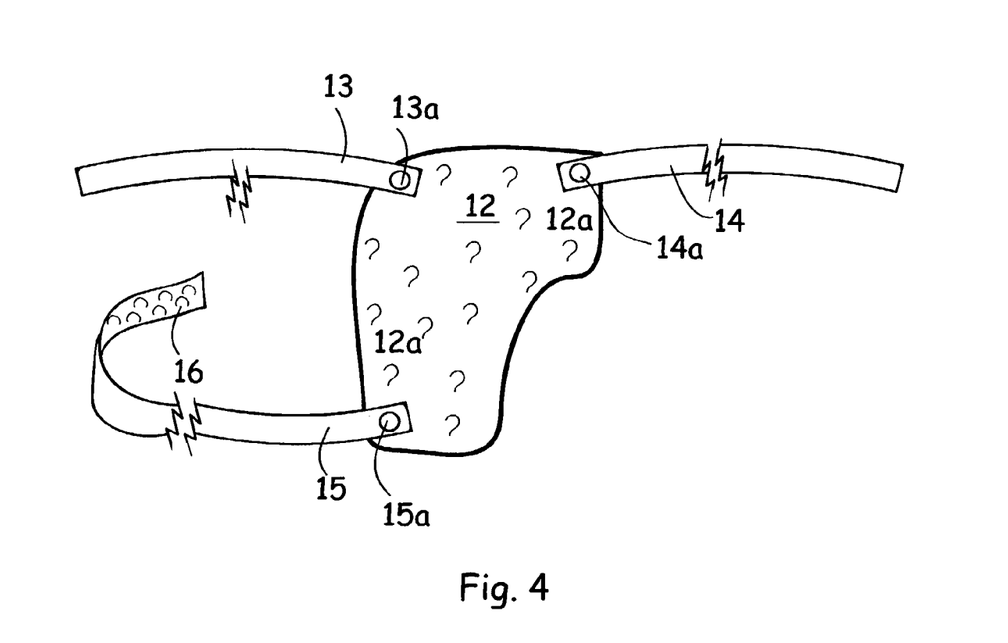
FIG. 4 shows a pad having straps thereon to be used on the inside of a hand.
Figure 5:
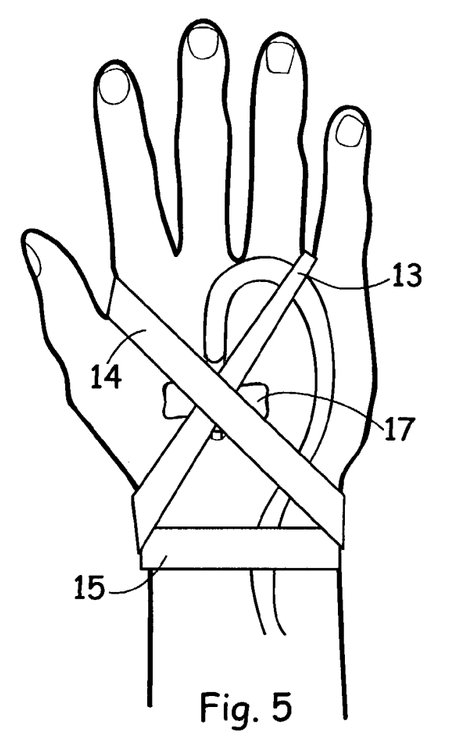
FIG. 5 shows a needle secured on the outside surface of a hand.
Figure 6:
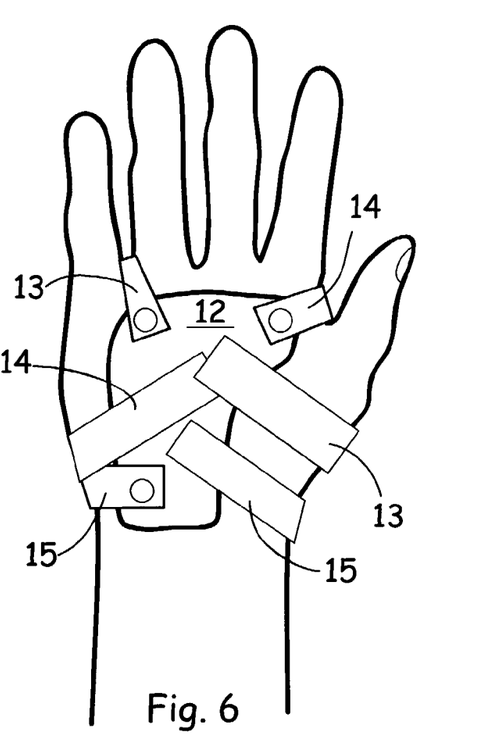
FIG. 6 shows the pad of FIG. 4 as it is applied to the inside of a hand including the straps as they are fastened.

FIG. 4 illustrates a pad 12 having three corners in a trian­gular shape where straps 13, 14 and 15 are applied. Again, the straps 13, 14 and 15 are fastened by way of grommets 13a, 14a and 15a, respectively, in a rotational manner as was explained with regard to FIG. 3, and have VELCRO™ loops on the surface facing pad 12 as exemplified by section 16 of strap 15. Again, the outer surface of the pad comprises hooks 12a of VELCRO™ as explained above. The pad 12 of FIG. 4 is used in the event when a needle is applied to the back of a hand as shown in FIGS. 5 and 6. The three straps 13, 14 and 15 are applied as shown in FIG. 5 where the straps 13 and 14 cross each other over a tab 17 and the strap 15 secures the implement around the wrist of the patient. FIG. 6 shows the implement of FIG. 5 as it is applied to the inside of the hand. The triangular shape of the pad 12 can clearly be seen in FIGS. 4 and 6.

Figure 7:
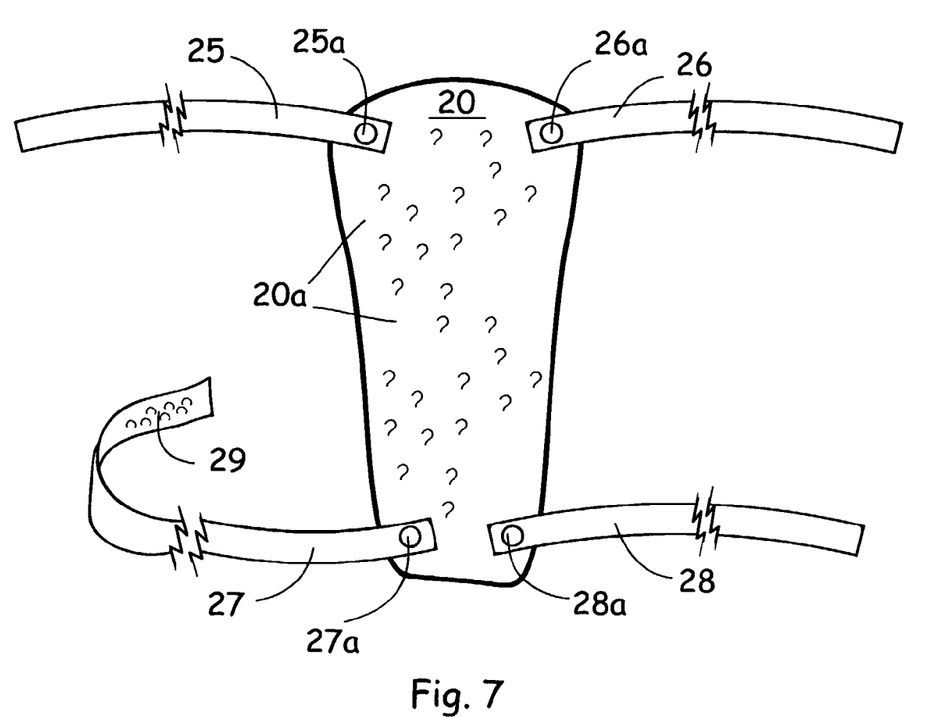
FIG. 7 illustrates a pad having straps thereon that is to be used on top of the wrist of a hand.
Figure 8:
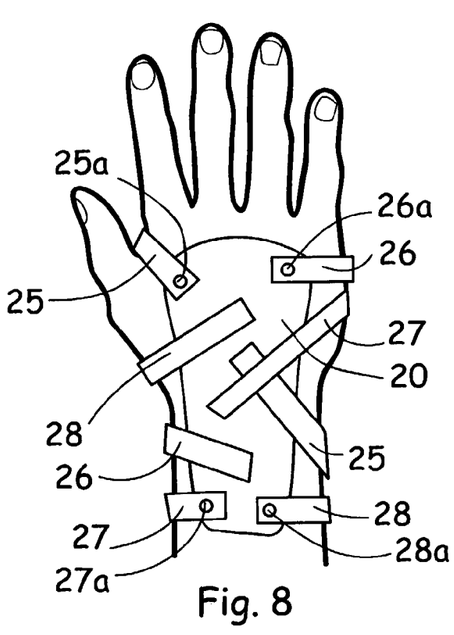
FIG. 8 illustrates the pad of FIG. 7 to show how the straps will wrap around the hand.
Figure 9:
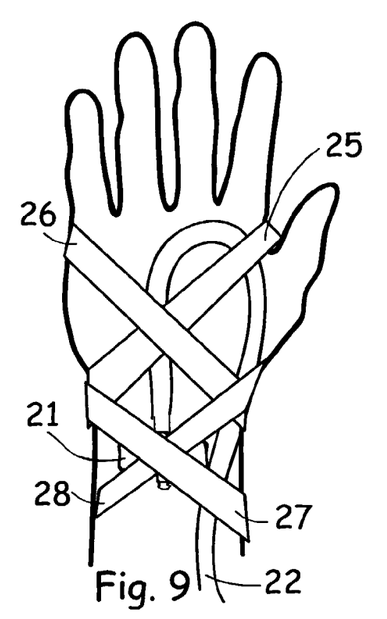
FIG. 9 illustrates a needle secured to the inside wrist of a hand.
Figure 9A:
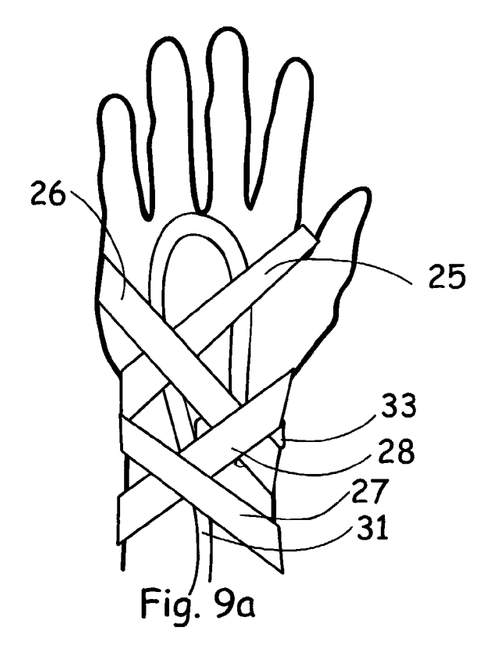
FIG. 9a illustrates a needle secured to the inside wrist of a hand in an alternate location to that depicted in FIG. 9.

FIG. 7 shows a different pad 20 of a substantially rectan­gular configuration having straps 25, 26, 27 and 28 fastened by way of grommets 25a, 26a, 27a and 28a, respectively, in a rotational manner as discussed in pads 11 and 12, and have VELCRO™ loops on the surface facing pad 20 as exempli­fied by section 29 of strap 27. The outer surface of the pad 20 comprises hooks 20a of VELCRO™ as explained above. One end of pad 20 is somewhat enlarged where the grommets 25a and 26a are located. This pad can be used when a needle is inserted on the inside wrist of a hand as can be seen in FIGS. 8, 9 and 9a. Referring first to FIGS. 8 and 9, the pad 20 is placed on the outside of the hand and the straps 27 and 28 cross each other over a tab 21 of a needle assembly 22. Straps 25 and 26 serve to additionally secure the pad 20 and the tube of needle assembly 22 to the hand. Referring now to FIG. 9a, this system will work perfectly well even if the IV is some­what offset from the middle of the wrist. The straps 26 and 28 cross over a tab 33 on an IV assembly 31. This is a somewhat complicated installation, but the cooperation between the pad 20 and the straps 25, 26, 27 and 28 makes for a versatile installation.

Figure 10:
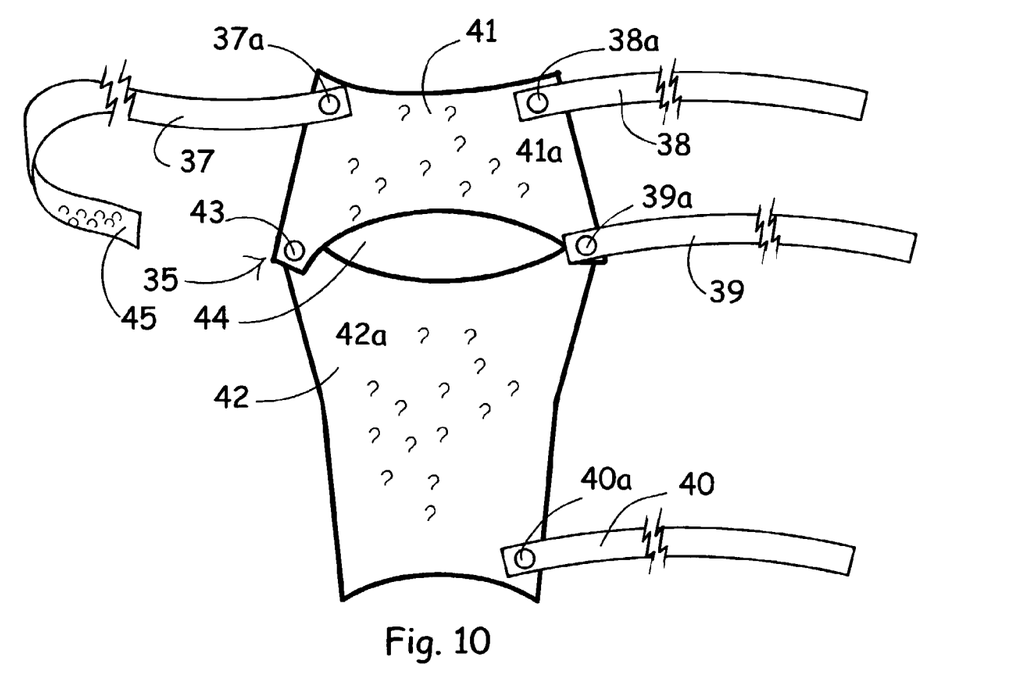
FIG. 10 shows a pad having straps thereon to be used on an elbow of an arm.
Figure 11:
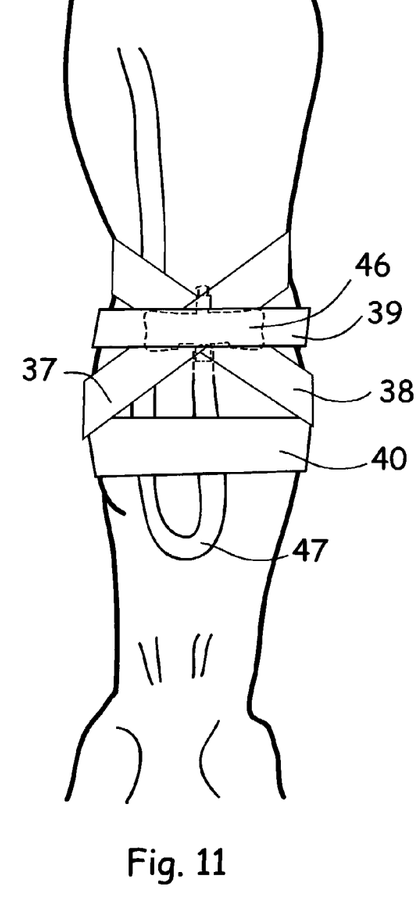
FIG. 11 shows a needle secured in the inside of an elbow.
Figure 12:
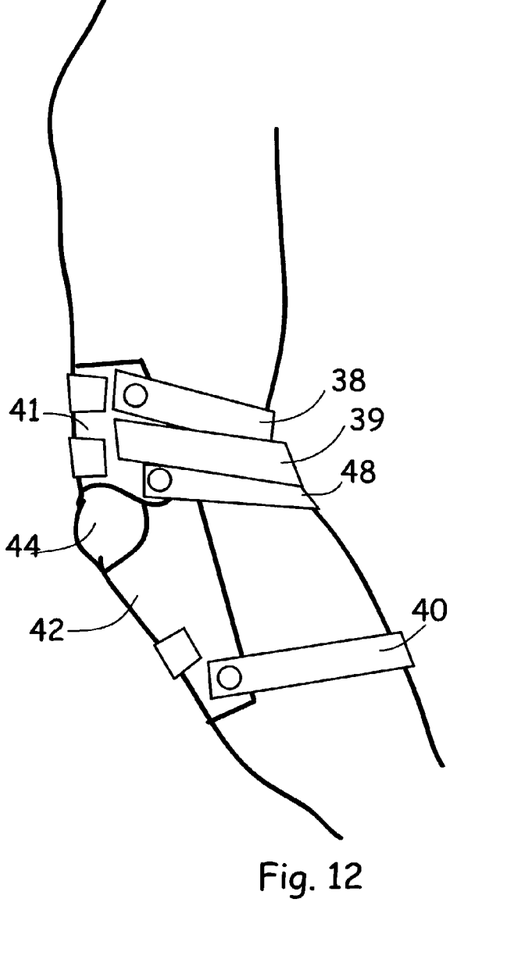
FIG. 12 illustrates the pad of FIG. 10 as it holds the needle of FIG. 11 in place.

FIG. 10 shows a yet a different pad 35 which can be installed at the elbow of a patient. This pad comes is particu­larly useful when a needle is to be inserted at the inside of the inner arm opposite an elbow. Pad 35 has straps 37, 38, 39 and 40 fastened by way of grommets 37a, 38a, 39a and 40a, respectively, in a rotational manner as discussed in pads 11, 12 and 20, and have VELCRO™ loops on the surface facing pad 35 as exemplified by section 45 of strap 37. The pad 35 is made up of two parts 41 and 42 having outer surfaces com­prising hooks 41a and 42a, respectively, of VELCRO™ as explained above. The parts 41 and 42 are connected by way of the grommets 43 and 39a. Grommet 39a is therefore fasten­ing together strap 39 and parts 41 and 42. The two parts 41 and 42 have opposing curved inner edges and when connected together leave an open space 44 which will fit around the elbow. The grommets 43 and 39a enable the parts 41 and 42 to rotate around each other so that once the pad is installed on the elbow, the two parts 41 and 42 will be able to move with the movement of the elbow. FIG. 11 shows the installation of the pad 35. FIGS. 11 and 12 show how the pad 35 and an IV assembly 47 having a tab 46 are held in place. To this end, the strap 40 circles the arm below the elbow while holding a loop of tube of assembly 47 in place. The straps 37 and 38 cross each other over the tab 46 while the strap 39 circles around the arm just above the elbow. This arrangement assures for a secure holding of the IV needle in place while at the same time affording visibility of the performance of the needle itself while the arm may rotate around the elbow.

The pad itself, in all of the above described installations, should be made of a semi-rigid material. That is, it should not give in any planar direction; yet, it should be bondable so that it can conform to any contours of an arm, hand, leg or other part of the body. The pad should not turn or flex with the different directions the straps may take. The grommets should allow the straps to turn relative to the pad. The application of two straps crossing over the needle assembly and tab thereof as described in the above installations, enables a first strap to apply a first pressure to initially secure and position said assembly, and a second strap to apply a second pressure further securing said assembly. As noted above, the pad can comprise hooks of the VELCRO™ fastening system, thereby allow the softer loops thereof to be used on the straps which face the patient. Patient comfort can be improved with this arrangement of the hooks and loops. Furthermore, the more compliant loops will better conform to the tabs of needle assemblies thereby providing for good retention thereof. Alternatively, the outer surface of the pad 11 could have the loops thereon so that the VELCRO™ system cannot snag on any outer garment. However, this arrangement would require the hooks to be applied to the straps and the previously men­tioned patient comfort and tab retention may be lessened as a result. In an alternative embodiment, adhesives could be used to attach the straps to the pads after wrapping said straps around the patient. In this embodiment, the adhesive could be applied such that it would not come into contact with the patient. This embodiment may be preferable when the device is to be disposed of after a single use. However, the VEL­CRO™ system may provide a more secure attachment of the straps to the pad than an adhesive. Furthermore, as noted above, the soft and compliant loops of the VELCRO™ sys­tem may provide for improved patient comfort and improved retention of the tabs of the needle assemblies.

As mentioned earlier, needles and cannulas are also referred to as venous access devices. The present invention can also be used with venous access device assemblies which do not have tabs, or as they are also called, wings or butterflies. Generally there will be a firm portion between the base of the needle or cannula and the tubing which is suitable for gripping or holding the venous access device assembly near the insertion point. A wing, butterfly, tab or said firm portion can be referred to as a stabilizing feature of the needle.

Given the benefit of the above disclosure of the present invention, those skilled in the art may envision how the present invention could be practiced using variations to the disclosed embodiments. For example, the present invention can be practiced and used to secure venous access devices to other locations of the body such as locations on the legs, and alternative pad shapes and strap arrangements can be envisioned, all without departing from the spirit and scope of the invention. Furthermore, the present invention can also be used to secure tubing and assemblies related to implanted venous catheters, which is yet another form of a venous access device. The foregoing detailed description should be regarded as illustrative rather than limiting and the appended claims, including all equivalents, are intended to define the scope of the invention.

What I claim is:

1. A method for securing intravenous needles to treatment sites which method comprises:

(a) providing a device for securing a plurality of intravenous needle assemblies wherein said needles include a tab, said device comprising: a semi-rigid but flexible pad capable of conforming to any contours of a patient's body and adapted to be installed on the opposite side of a part of a patient's body near an injection site, said pad having upper and lower flexible straps installed thereon in the periphery of said pad by fastening means, said straps, when crossing each other in a first location opposite said pad, will trap a holding tab of said intravenous needle assembly while said straps continue around said patient's part near an injection site to be fastened to said pad, means for separably fastening said straps to said pad after surrounding said patient's part near an injection site, and wherein said fastening means allow said straps to rotate relative to said pad for securing said plurality of needles without blocking the needle injection site;

(b) installing said device as defined in step (a) to the opposite side of a part of a patient's body near an injection site requiring attachment of intravenous needles; and (c) fastening the straps of said device as defined in step (a).

* * * * *